US006177091B1

(12) United States Patent
Bara et al.

(10) Patent No.: US 6,177,091 B1
(45) Date of Patent: Jan. 23, 2001

(54) NON-MIGRATING MAKE-UP OR CARE COMPOSITION CONTAINING AN ORGANOPOLYSILOXANE AND A FATTY PHASE

(75) Inventors: Isabelle Bara, Paris; Frédéric Auguste, Chevilly-Larue, both of (FR)

(73) Assignee: L'Oreal, Paris (FR)

( * ) Notice: Under 35 U.S.C. 154(b), the term of this patent shall be extended for 0 days.

(21) Appl. No.: 08/994,989

(22) Filed: Dec. 19, 1997

(30) Foreign Application Priority Data

Dec. 24, 1996 (FR) .................................. 96 15985

(51) Int. Cl.$^7$ ............................. A61K 6/00; A61K 7/00; A61K 7/04
(52) U.S. Cl. ............................. 424/401; 424/61
(58) Field of Search .................... 424/401, 61; 514/844, 514/845

(56) References Cited

U.S. PATENT DOCUMENTS

| | | | |
|---|---|---|---|
| 4,980,167 | 12/1990 | Harashima et al. | 424/401 |
| 5,266,321 | * 11/1993 | Shukuzaki et al. | 424/401 |

FOREIGN PATENT DOCUMENTS

| | | |
|---|---|---|
| 61-194009 | 8/1986 | (JP) . |
| 1-250306 | 10/1989 | (JP) . |
| 1-250307 | 10/1989 | (JP) . |
| 2-243612 | 9/1990 | (JP) . |
| 7-258028 | 10/1995 | (JP) . |
| 7-267820 | 10/1995 | (JP) . |
| 8-301727 | 11/1996 | (JP) . |
| 8-319215 | 12/1996 | (JP) . |
| 9-143029 | 6/1997 | (JP) . |
| 9-175939 | 7/1997 | (JP) . |
| 9-175940 | 7/1997 | (JP) . |
| 9-315936 | 12/1997 | (JP) . |
| 9-328409 | 12/1997 | (JP) . |
| 10-194931 | 7/1998 | (JP) . |

OTHER PUBLICATIONS

*Dictionary of Plastics*, Keizo Miyasaka, ed., Akura Pub. Co., Ltd., 1992, pp. 285–286.
JPO Notice of Reasons for Rejection, for corresponding Japanese Patent Application Hei 9–355839, Mailing No. 265611 (Dec. 7, 1999).
JPO Written Directive for corresponding Japanese Patent Application Hei 9–355839, Mailing No. 265612 (Dec. 7, 1999).
Chemical Abstracts, vol. 126, No. 8, Abstract No. 108664 (1997).
Chemical Abstracts, vol. 124, No. 4, Abstract No. 37392 (1996).

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

A non-migrating composition containing a solid, partially crosslinked, elastomeric organopolysiloxane and a fatty phase containing at least one non-volatile oil and at least one wax, particularly for the care or make up the lips and the face. This composition is gentle to apply, spreads easily, is non-sticky and does not dry the skin or the lips.

25 Claims, No Drawings

NON-MIGRATING MAKE-UP OR CARE COMPOSITION CONTAINING AN ORGANOPOLYSILOXANE AND A FATTY PHASE

The technology involved in this application is related to that disclosed in the following co-pending U.S. applications, filed on even date herewith:
(1) Title: Composition Comprising an Organopolysiloxane Gel
Inventor: Isabelle Bara
Attorney Docket No.: 05725.0260
(2) Title: Transfer-Free Make-up or Care Composition Containing an Organopolysiloxane and a Fatty Phase
Inventors: Isabelle BARA and Fryédérich AUGUSTA
Attorney Docket No.: 05725.0267

The specifications of these related applications are hereby specifically incorporated by reference The present invention relates to a make-up and/or care composition for human skin and/or lips, and in particular to a lip coloring composition or a foundation, in the form of a stick, a cupel or a cream containing an organopolysiloxane.

The known lipstick and foundation compositions generally comprise fatty substances such as oils, pasty compounds and waxes, as well as a particulate phase generally composed of fillers and pigments.

In standard lipsticks, the oils impart a large part of the properties of these lipsticks, such as the ease of application, the slippery properties and the sheen. In addition, most of these oils, and in particular the plant oils, give the lipsticks treating properties. This is likewise the case for foundations.

Unfortunately, when they are applied to the skin or the lips, these make-up compositions, and especially the pigments in these compositions, tend to migrate, that is to say to travel inside the wrinkles and fine lines in the skin around the lips and the eyes, giving rise to an aesthetically unpleasant effect. The appearance of these traces tends to put certain consumers off from using this type of make-up.

A subject of the present invention is a make-up or care composition which makes it possible to overcome these drawbacks and makes it possible, in particular, to obtain a film which does not migrate and which has cosmetic properties such as, in particular, slippery properties and properties of not causing tautness and not drying the lips or the skin.

The invention applies not only to make-up products for the lips but also to care and/or treating products for the lips, as well as to make-up, care and/or treating products for the skin.

More specifically, the subject of the invention is a non-migrating make-up or care composition containing at least one solid, at least partially crosslinked, elastomeric organopolysiloxane as gelling agent, combined with a fatty phase containing at least one oil and at least one wax, and a particulate filler.

The term "elastomeric" is understood to refer to a supple, deformable material having viscoelastic properties and in particular the consistency of a sponge or of a supple sphere.

The elastomeric organopolysiloxanes of the composition of the invention have noteworthy oil-gelling power. They do not dry the skin and afford good cosmetic properties. These novel elastomers lead to compositions which are comfortable when applied, soft and non-sticky to touch. This softness is due, on the one hand, to the texture of the organopolysiloxanes and, on the other hand, to their properties, which are comparable to those of microsponges trapping volatile oils. In addition, by virtue of the trapping of the oils in the organopolysiloxane, the compositions of the invention no longer migrate in the wrinkles and fine lines in the skin, even when they contain treating oils.

The compositions of the invention may be in the form of a paste, a solid or a cream. They may be an oil-in-water or water-in-oil emulsion, or a solid or supple anhydrous gel.

The elastomeric organopolysiloxanes in accordance with the invention are partially or totally crosslinked and of three-dimensional structure. When included in a fatty phase, they become converted, depending on the fatty phase content used, from a product of spongy appearance when they are used in the presence of low fatty phase contents, into a homogeneous gel in the presence of larger amounts of fatty phase. Gelling of the fatty phase by these elastomers may be total or partial.

The elastomers of the invention are generally conveyed in the form of a gel including an elastomeric organopolysiloxane of three-dimensional structure, and further including at least one hydrocarbon oil and/or a silicone oil.

The elastomeric organopolysiloxanes according to the invention may be selected from the crosslinked polymers described in European patent application EP-A-0,295,886, the disclosure of which is specifically incorporated by reference herein. According to that application, they are obtained by addition reaction and crosslinking, in the presence of a platinum-type catalyst, of at least:
(a) an organopolysiloxane having at least two $C_2$–$C_6$ lower alkenyl groups per molecule; and
(b) an organopolysiloxane having at least two hydrogen atoms linked to a silicon atom per molecule.

The elastomeric organopolysiloxanes according to the invention may also be selected from those described in U.S. Pat. No. 5,266,321, the disclosure of which is specifically incorporated by reference herein. According to that patent, they are selected in particular from:
i) organopolysiloxanes comprising $R_2SiO$ and $RSiO_{1.5}$ units and optionally $R_3SiO_{0.5}$ and/or $SiO_2$ units in which the radicals R, independently of each other, represent a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1:1 to 30:1;
ii) organopolysiloxanes which are insoluble and swellable in silicone oil, obtained by addition of an organohydrogenopolysiloxane (1) and of an organopolysiloxane (2) having unsaturated aliphatic groups such that the amount of hydrogen or of unsaturated aliphatic groups in (1) and (2) respectively ranging from 1 to 20 mol % when the organopolysiloxane is non-cyclic and from 1 to 50 mol % when the organopolysiloxane is cyclic.

The organopolysiloxanes of the composition of the invention are, for example, those marketed under the names KSG6 from Shin-Etsu, TREFIL E-505C or TREFIL E-506C from Dow-Coming, GRANSIL from Grant Industries (SR-CYC, SR DMFI10, SR-DC556) or those marketed in the form of preconstituted gels (KSG15, KSG17, KSG16, KSG18 from Shin-Etsu, GRANSIL SR 5CYC gel, GRANSIL SR DMF 10 gel, GRANSIL SR DC556 gel, SF 1204 and JK 113 from General Electric). A mixture of these commercial products may also be used.

The organopolysiloxane is preferably present in the organopolysiloxane/fatty phase mixture in the form of a more or less homogeneous gel at a concentration ranging from 0.3 to 40% of the total weight of the composition. Preferably, the elastomer represents, as active material, from 0.1 to 20% in the composition and more preferably from 0.3 to 15%.

The fatty phase may be of any nature; it contains oils (products which are fluid at room temperature) which may be silicone, fluoro, fluorosilicone or hydrocarbon oils which are optionally partially siliconated. The best gelling is achieved with silicone oils or partially siliconated oils, apolar oils and sparingly polar oils and a few polar oils which do not harm the stability of the system. These oils are determined in particular as a function of their solubility parameters, defined in the Hansen space.

In particular, the composition of the invention comprises non-volatile oils used conventionally in the field of application envisaged, and waxes.

As non-volatile oils which may be used in the invention, mention may be made, in particular, of:

hydrocarbon oils of animal origin such as perhydrosqualene;

plant hydrocarbon oils such as liquid triglycerides of fatty acids, for example sunflower oil, corn oil, soybean oil, marrow oil, grapeseed oil, sesame oil, hazelnut oil, apricot oil, macadamia oil, castor oil, avocado oil, caprylic/capric acid triglycerides such as those sold by the company Stearineries Dubois or those sold under the names MIGLYOL 810, 812 and 818 by the company Dynamit Nobel;

oils of formula $R_9COOR_{10}$ in which $R_9$ represents a higher fatty acid residue containing from 7 to 19 carbon atoms and $R_{10}$ represents a branched hydrocarbon chain containing from 3 to 20 carbon atoms, such as, for example, Purcellin oil;

linear or branched hydrocarbons of mineral or synthetic origin, such as non-volatile liquid paraffins and derivatives thereof, petroleum jelly, polydecenes, and hydrogenated polyisobutene such as parleam;

synthetic esters and ethers such as isopropyl myristate, octanoates, decanoates or ricinoleates of alcohols or of polyalcohols;

fatty alcohols such as octyidodecanol or oleyl alcohol;

partially hydrocarbonated and/or siliconated fluoro oils such as those described in Japanese patent document JP-A-2-295912, the disclosure of which is specifically incorporated by reference herein;

silicone oils such as linear, non-volatile polymethylsiloxanes (PDMS) which are liquid or pasty at room temperature, phenyidimethicones, phenyltrimethicones and polymethylphenylsiloxanes;

mixtures thereof.

The oils represent from 5 to 80% of the total weight of the composition, preferably from 20 to 70% and better still from 30 to 50%. In particular, the non-volatile oils represent from 4 to 60%, and better still from 30 to 50%, of the total weight of the composition, the volatile oils in this case representing the remainder.

The waxes in the compositions of the invention are hydrocarbon, fluoro or silicone waxes or mixtures of waxes, which may be solid or semi-solid (in the form of a paste) at room temperature. These waxes may be of plant, mineral, animal and/or synthetic origin. In particular, these waxes have a melting point of greater than 25° C. and, better still, greater than 45° C.

The silicone waxes may be waxes having a silicone structure and units containing one or more pendant alkyl or alkoxy chains and/or alkyl or alkoxy chains at the end of the silicone structure, these chains being linear or branched and containing from 10 to 45 carbon atoms. These waxes are respectively known as aklyldimethicones and alkoxydimethicones. Moreover, these alkyl chains may contain one or more ester functions.

Among the silicone waxes which may be used in the invention, mention may be made of behenoxydimethicone, such as that sold by Goldschmidt under the name Abil Wax 2440; stearyldimethicone, such as that sold by Dow Corning under the name DC 2503; cetyldimethicone, such as that sold by Goldschmidt under the name Abil Wax 9814; stearylmethicone, such as that sold by Goldschmidt under the name Abil Wax 9809; $C_{24}$–$C_{28}$ alkyldimethicone, such as that sold by Goldschmidt under the name Abil Wax 9810; $C_3$–$C_{45}$ alkylmethicone, such as that sold by Goldschmidt under the name Abil Wax 9811; stearoxydimethicone, such as that sold by Goldschmidt under the name Abil Wax 2434; dimethicone behenate, such as that sold by Rhône Poulenc under the name Myrasil Wax B.

As other silicone waxes which may be used in the invention, mention may be made of alkyldimethicone copolymers. These copolymers are especially those described in European patent application EP-A-527,594, U.S. Pat. No. 5,061,481 and U.S. Pat. No. 5,397,566. Mention may also be made of silicone waxes modified with fluoro chains, such as those described in European patent application EP-A-661,042.

As other waxes which may be used in the invention, mention may be made of waxes of animal origin such as lanolin, beeswax; plant waxes, such as carnauba wax or candelilla wax; mineral waxes, for example paraffin wax, lignite wax or microcrystalline waxes, ceresine or ozokerite; synthetic waxes such as polyethylene waxes.

The nature of the waxes and the oils, as well as the amounts thereof, may be selected in various ways by a person skilled in the art in order to prepare a composition having the desired cosmetic properties, in particular of consistency or of texture.

In particular, the presence of a large amount of waxes makes it possible to ensure good mechanical strength, in particular when the composition is in the form of a stick.

In general, the composition may comprise wax in a proportion of 1 to 50% of the total weight of the composition, and preferably from 10 to 30%.

In addition to the oils and waxes described above, the fatty phase may contain one or more oils which are volatile at room temperature. The term volatile oil is understood to refer to an oil which can evaporate on contact with the skin or the lips.

These volatile oils may be hydrocarbon oils, silicone oils or mixtures thereof. The volatile silicones are, for example, silicones containing a linear silicone structure and units with a pendant alkyl chain and/or an alkyl chain at the end of the silicone structure, these alkyl chains being linear or branched and containing from 3 to 10 carbon atoms. The volatile silicones with an alkyl chain especially have the formula (1) below:

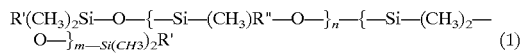
(1)

in which:

R' and R" represent, independently, H, methyl or a chain having from 3 to 10 carbon atoms, n and m represent integers ranging from 0 to 10, with the proviso that if R' is hydrogen or methyl, n is not 0 and R" represents an alkyl chain of 3 to 10 carbon atoms. As alkylated volatile silicones which may be used in the invention, mention may be made of alkyl heptamethyltrisiloxanes with a $C_4$, $C_5$, $C_6$, $C_7$ or $C_8$ alkyl group, such as, for example, hexylheptamethyltrisiloxane of formula: $(CH_3)_3$—Si—O—Si$(CH_3)(C_6H_{13})$—O—Si—$(CH_3)_3$;

octylheptamethyltrisiloxane of formula: $(CH_3)_3$—Si—O—Si$(CH_3)(C_8H_{15})$—O—Si$(CH_3)_3$; and mixtures thereof.

As volatile silicones which may be used in the invention, mention may also be made of polydimethylsiloxanes with a linear chain having from 2 to 6 silicon atoms. These silicones satisfy formula (1) with m having a value of 0, n having a value from 0 to 6 and R' and R" simultaneously represent $CH_3$ or phenyl. Mention may be made, for example, of methylpolysiloxanes such as hexamethyldisiloxane, methylphenylpolysiloxanes, ethylpolysiloxanes, ethylmethylpolysiloxanes, ethylphenylpolysiloxanes, hydroxymethylpolysiloxanes and mixtures thereof.

Cyclic silicones having from 3 to 7 units —$R_1R_2SiO$—, with $R_1$ and $R_2$ independently representing H, methyl, ethyl or phenyl, may also be used as volatile silicones. Mention may be made, for example, of octamethylcyclopentasiloxane, decamethylcyclopentasiloxane or mixtures thereof.

As volatile hydrocarbon oils which may be used in the invention, mention may be made of $C_3$ to $C_{20}$ isoparaffins, for instance the $C_{12}$ isoparaffin known as isododecane and $C_{16}$ isoparaffin, for instance isohexadecane.

The composition of the invention may also comprise any additive commonly used in the field concerned, such as water-soluble or liposoluble dyes, antioxidants, essential oils, preserving agents, cosmetic or dermatological active agents, moisturizers, vitamins, essential fatty acids, lipophilic sunscreens, and liposoluble polymers, in particular hydrocarbons such as polyalkylenes. These additives may preferably be present in the composition in a proportion of from 0 to 20% of the total weight of the composition, and more preferably from 0 to 10%.

Obviously, a person skilled in the art will take care to select the optional complementary additives and/or the amount thereof such that the advantageous properties of the composition according to the invention are not, or are not substantially, adversely affected by the addition envisaged. In particular, these additives must not harm the homogeneity, the stability, the comfort or the "non-migrating" nature of the composition.

The compositions according to the invention may especially be in the form of a stick or tube or in the form of a supple or cast paste, or alternatively in the form of a gelled oily liquid or a cream.

The composition according to the invention may be in the form of a colored make-up product for the skin, in particular a foundation, a blusher, an eyeshadow, a concealer stick or make-up for the lips such as a lipstick. It may also be in non-colored form, optionally containing cosmetic or dermatological active agents. In this case, it may be used as a care base for the lips (lip balms for protecting the lips against the cold and/or the sun and/or the wind) or a fixing base to be applied over a standard lipstick. The fixing base thus forms a protective film over the film of lipstick, which limits its migration.

The composition of the invention may also be in the form of a dermatological or skincare composition, or in the form of an antisun composition.

Obviously, the composition of the invention must be cosmetically or dermatologically acceptable, that is to say non-toxic and capable of being applied to human skin or mucous membranes (lips, inner edge of the eyelids).

Preferably, the composition of the invention may comprise a particulate phase which is preferably present in a proportion of from 0 to 35% of the total weight of the composition, more preferably from 5 to 25%, and which may comprise pigments and/or pearlescent agents and/or fillers usually used in cosmetic compositions.

The term pigments should be understood to mean white or colored, inorganic or organic particles which are insoluble in wax and volatile silicone, intended to color and/or opacify the composition. The term charges should be understood to mean colorless or white, inorganic or synthetic, lamellar or non-lamellar particles. The term pearlescent agents should be understood to mean iridescent particles, in particular those produced by certain molluscs in their shell or synthesized. These fillers and pearlescent agents serve to modify the texture of the composition as well as the matte effect/sheen.

The pigments may preferably be present in the composition in a proportion of from 0 to 25% of the weight of the final composition, and more preferably in a proportion of 5 to 15%. As inorganic pigments which may be used in the invention, mention may be made of titanium oxide, zirconium oxide or cerium oxide, as well as zinc oxide, iron oxide or chromium oxide and ferric blue. Among the organic pigments which may be used in the invention, mention may be made of carbon black and barium, strontium, calcium and aluminum lakes.

The pearlescent agents may preferably be present in the composition in a proportion of from 0 to 20% of the total weight of the composition, more preferably in a high content of about 8 to 15%. Among the pearlescent agents which may be used in the invention, mention may be made of mica coated with titanium oxide, with iron oxide, with natural pigment or with bismuth oxychloride such as colored titanium mica.

The fillers may preferably be present in a proportion of from 0 to 35% of the total weight of the composition, more preferably 5 to 15%. Mention may be made in particular of talc, mica, silica, kaolin, nylon powders (in particular ORGASOL), polyethylene powders, Teflon, starch, boron nitride, copolymer microspheres such as EXPANCEL (Nobel Industrie), polytrap (Dow Corning) and silicone resin microbeads (TOSPEARL from Toshiba, for example).

More precisely, the subject of the invention is an anhydrous, non-migrating lipstick or foundation, characterized in that it contains at least one solid, at least partially crosslinked, elastomeric organopolysiloxane as gelling agent, combined with a fatty phase containing at least one oil and at least one wax, and a pigmentary filler.

The composition according to the invention may be manufactured by heating one or more elastomeric organopolysiloxanes combined with one or more oils, one or more waxes, one or more pigments, one or more fillers and/or one or more other additives at a temperature above the highest melting point of the waxes, after which the molten mixture is cast in a mold. This process makes it possible to obtain a composition in the form of a solid stick or cupel.

The composition may also be obtained by extrusion as described in European patent application EP-A-667,146. This process involves blending the paste (waxes+oils+additives+pigments) during the cooling phase in order to create in the bulk zones for crushing the paste using a cylinder mill or a screw extruder-mixer. This process makes it possible to obtain a composition in the form of a soft paste.

The subject of the invention is also the use of a solid, at least partially crosslinked, elastomeric organopolysiloxane, as gelling agent, in a make-up or care composition for a region of human skin or lips, in order to reduce the migration of the composition around the region or the lips.

The subject of the invention is also a process for limiting and/or preventing the migration of a make-up or care composition for the skin or the lips, this process involving introducing at least one solid, at least partially crosslinked, elastomeric organopolysiloxane into the composition.

The subject of the invention is also a cosmetic or dermatological treatment process for human skin or lips, this process involving applying a cosmetic composition as defined above to the skin or the lips.

The invention is illustrated in greater detail in the example which follows. The example is in no way limiting. The percentages are given on a weight basis.

EXAMPLE 1

| | |
|---|---|
| Polyethylene wax | 15.0% |
| Crosslinked organopolysiloxane at a concentration of 60% in a non-volatile PDMS (KSG6) | 10.0% |
| Phenyltrimethicone (oil) | 25.0% |
| Stearyldimethicone (pasty) | 30.0% |
| Lanolin | 10.0% |
| Pigments | 10.0% |

This composition was obtained by swelling the organopolysiloxane in the oils at room temperature. The pigments were then impasted in the gel obtained, at 60° C., after which the mixture was ground in a three-cylinder mill at room temperature. The ground product was mixed with the wax and with the pasty material, at 95° C., and was then cast in a suitable mold. A stick of lipstick with a pleasant texture, which spread well and did not migrate over time after it was applied to the lips, was thus obtained. The obtained film was glossy.

The composition of example 1 (C1) was compared to an example C2 containing the same ingredients as those of C1, but without the organopolysiloxane. These compositions, C1 and C2, were applied on halflips by beauticians. Composition C1 was judged by all of the test participants as having similar cosmetic properties as composition C2, but with less migration.

We claim:

1. A process for limiting and/or preventing the migration of a human lips and/or skin make-up or care composition inside the wrinkles and/or fine lines of the skin around the lips and/or eyes, comprising applying a composition comprising at least one solid, at least partially crosslinked, elastomeric organopolysiloxane combined with a fatty phase comprising at least one oil and at least one wax to said skin and/or lips.

2. A process according to claim 1, wherein said elastomeric organopolysiloxane is obtained by addition reaction and crosslinking, in the presence of a catalyst, of at least:
   (a) an organopolysiloxane having at least two $C_2$–$C_6$ lower alkenyl groups per molecule; and
   (b) an organopolysiloxane having at least two hydrogen atoms linked to a silicon atom per molecule.

3. A process according to claim 1, wherein said elastomeric organopolysiloxane is:
   (i) an organopolysiloxane comprising $R_2SiO$ and $RSiO_{1.5}$ units and optionally $R_3SiO_{0.5}$ and/or $SiO_2$ units wherein the radicals R, independently of each other, represents a hydrogen, an alkyl, an aryl, an unsaturated aliphatic group, wherein the weight ratio of said $R_2SiO$ units to said $RSiO_{1.5}$ units ranges from 1:1 to 30:1; or
   (ii) an organopolysiloxane which is insoluble in silicone oil, obtained by addition of an organohydrogenopolysiloxane and of an organopolysiloxane having unsaturated aliphatic groups, wherein the amount of hydrogen or of unsaturated aliphatic groups in said organohydrogenopolysiloxane and said organopolysiloxane respectively ranges from 1 to 20 mol % when the organopolysiloxane is non-cyclic and from 1 to 50 mol % when the organopolysiloxane is cyclic.

4. A process according to claim 1, wherein said elastomeric organopolysiloxane is present in the form of a homogeneous gel at a concentration ranging from 0.3 to 40% by weight relative to the total weight of said make-up or care composition.

5. A process according to claim 1, wherein said elastomeric organopolysiloxane is present in the form of a homogeneous gel at a concentration ranging from 0.1 to 20% by weight relative to the total weight of said make-up or care composition.

6. A process according to claim 1, wherein said elastomeric organopolysiloxane is present in the form of a homogeneous gel at a concentration ranging from 0.3 to 15% by weight relative to the total weight of said make-up or care composition.

7. A process according to claim 1, wherein said at least one oil is a non-volatile oil.

8. A process according to claim 7, wherein said non-volatile oil is:
   a hydrocarbon oil of animal or plant origin;
   an oil of formula $R_9COOR_{10}$ wherein $R_9$ represents a higher fatty acid residue containing from 7 to 19 carbon atoms and $R_{10}$ represents a branched hydrocarbon chain containing from 3 to 20 carbon atoms;
   a linear or branched hydrocarbon of mineral or synthetic origin;
   a fatty alcohol;
   a synthetic ester or a synthetic ether;
   a linear polymethylsiloxane;
   a silicone oil; or
   a fluoro oil which is optionally partially hydrocarbonated and/or siliconated.

9. A process according to claim 8, wherein said silicone oil is a linear, non-volatile polymethylsiloxane which is liquid or pasty at room temperature; a phenyldimethicone; a phenyltrimethicone; or a polymethylphenylsiloxane.

10. A process according to claim 1, wherein, wherein said at least one oil is present in an amount ranging from 5 to 80% by weight relative to the total weight of said composition.

11. A process according to claim 10, wherein said at least one oil is present in an amount ranging from 20 to 70% by weight relative to the total weight of said composition.

12. A process according to claim 11, wherein said at least one oil is present in an amount ranging from 30 to 50% by weight relative to the total weight of said composition.

13. A process according to claim 1, wherein said at least one wax is a hydrocarbon, fluoro or silicone wax.

14. A process according to claim 1, wherein said at least one wax present in a concentration ranging up to 50% by weight relative to the total weight of said make-up or care composition.

15. A process according to claim 14, wherein the concentration of said wax ranges from 10 to 30% by weight relative to the total weight of said make-up or care composition.

16. A process according to claim 1, wherein said make-up or care composition further comprises a particulate phase.

17. A process according to claim 16, wherein said particulate phase is present in a concentration ranging up to 35% by weight relative to the total weight of the make-up or care composition.

18. A process according to claim 12, wherein said particulate phase is present in a concentration ranging from 5 to 25% by weight relative to the total weight of the make-up or care composition.

19. A process according to claim 1, wherein said make-up or care composition is in the form of a paste, a solid, a cream, an oil-in-water emulsion, a water-in-oil emulsion or an anhydrous gel.

20. A process according to claim 1, wherein said make-up or care composition is in the form of a stick or tube, a supple or cast paste, a cream or a gelled oily liquid.

21. A process according to claim 1, wherein said make-up or care composition further comprises at least one cosmetic or dermatological active agent.

22. A process according to claim 1, wherein said make-up or care composition is in the form of a foundation, a blusher, an eyeshadow, a concealer product, a lip coloring composition, a care base or a fixing base for the lips, a dermatological product or skincare product or an antisun composition.

23. A process for limiting and/or preventing the migration of a human lips and/or skin make-up or care composition inside the wrinkles and/or fine lines of the skin around the lips and/or eyes, said process comprising introducing at least one solid, at least partially crosslinked, elastomeric organopolysiloxane into said composition.

24. A process for limiting and/or preventing the migration of a human lips and/or skin make-up or care composition inside the wrinkles and/or fine lines of the skin around the lips and/or eyes, comprising applying a colored composition containing at least one solid, at least partially crosslinked elastomeric organopolysiloxane combined with a fatty phase comprising at least one oil and at least one wax to said skin and/or lips.

25. A process according to claim 24, wherein said colored composition is chosen from foundations, blushers, eyeshadows, concealers, and lip products.

* * * * *

UNITED STATES PATENT AND TRADEMARK OFFICE
CERTIFICATE OF CORRECTION

PATENT NO. : 6,177,091 B1
DATED : January 23, 2001
INVENTOR(S) : Bara et al.

It is certified that error appears in the above-identified patent and that said Letters Patent is hereby corrected as shown below:

Claim 18, column 9, 1.3,
Change "claim 12" to -- claim 17 --.

Signed and Sealed this

Twenty-third Day of October, 2001

Attest:

NICHOLAS P. GODICI
Attesting Officer
Acting Director of the United States Patent and Trademark Office